United States Patent [19]

Cetlin

[11] Patent Number: 4,741,696
[45] Date of Patent: May 3, 1988

[54] ORTHODONTIC APPLIANCES FOR DENTAL ARCH EXPANSION

[75] Inventor: Norman Cetlin, Newton, Mass.

[73] Assignee: GAC International, Inc., Central Islip, N.Y.

[21] Appl. No.: 911,408

[22] Filed: Sep. 25, 1986

[51] Int. Cl.[4] ............................................. A61C 7/00
[52] U.S. Cl. .......................................... 433/7; 433/17
[58] Field of Search ................................... 433/7, 5, 17

[56] References Cited

U.S. PATENT DOCUMENTS

| | | | |
|---|---|---|---|
| 1,773,588 | 8/1930 | Linde | 433/7 |
| 3,792,529 | 2/1974 | Goshgarian | 433/7 |
| 4,373,913 | 2/1983 | McAndrew | 433/7 |
| 4,408,989 | 10/1983 | Cleary | 433/7 |
| 4,592,725 | 6/1986 | Goshgarian | 433/7 |

OTHER PUBLICATIONS

Ormco Catalogue, p. 43, Feb. 14, 1963, "Buccal Tubes".

Primary Examiner—Robert Peshock
Attorney, Agent, or Firm—Kenyon & Kenyon

[57] ABSTRACT

A system of orthodontic appliances and method for their use for gaining space in a dental arch without extraction. Space is gained in the maxillary arch primarily through a transpalatal bar, transmitting force to selected teeth through a maxillary lingual sheath, the receiving portion of the sheath having a mesial offset of about eight degrees. Additional space in the maxillary arch may be gained by employing an extraoral force appliance, transmitting force through a maxillary buccal tube carried on a selected pair of maxillary molars. The mandibular arch is treated by applying similar forces to selected molars through a lip bumper. This appliance transmits force through a mandibular buccal tube that receives the bumper in a passage having a mesial offset of about five degrees. The mandibular buccal tube also carries an archwire receiving passage, distally offset by about four degrees.

10 Claims, 5 Drawing Sheets

FIG. 5
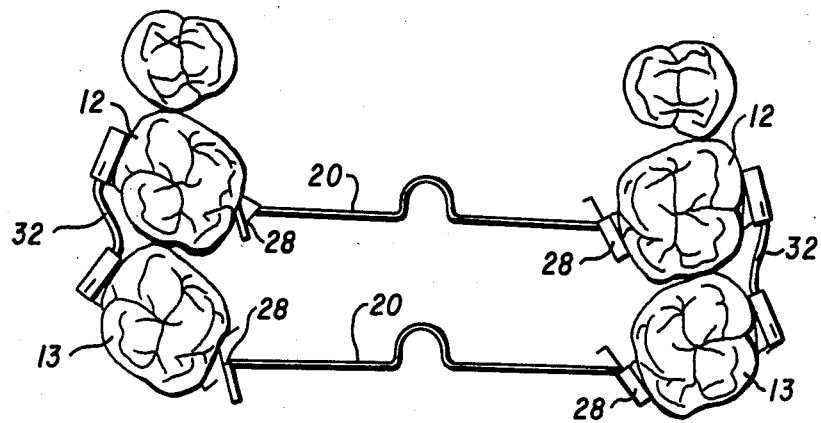
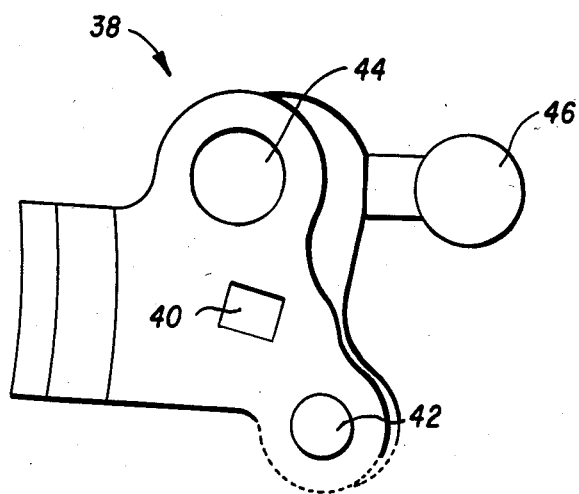
FIG. 6

ORTHODONTIC APPLIANCES FOR DENTAL ARCH EXPANSION

BACKGROUND OF THE INVENTION

This invention is related to the art of orthodontics, and more particularly to the art of achieving proper alignment of the dental arch through forces applied to selected teeth by orthodontic applicances.

The practice of orthodontics is concerned not merely with the aesthetic alignment and appearance of teeth, but primarily addresses the proper positioning of teeth in relation to the bony structure of the face. For an individual facial structure, one can construct the optimum formation of the maxillary and mandibular arches, and the degree of an individual's orthodontic malformation can be related to the departure from those optima. In general, orthodontic practice seeks to realign teeth to form arches closely resembling the optimum shapes.

Because many patients exhibit dental "crowding"—the eruption of teeth in a portion of the arch too small to accomodate them naturally—conventional treatment regimes generally call for the extraction of four teeth (usually the first bicuspids) as an initial step. Those in the art justify this procedure by the requirement to allow sufficient space in which to realign the remaining teeth.

It has been found, however, that long term problems can stem from such extraction. First, relapse can occur, given the relatively long distances over which some teeth are moved within the arch. Second, such extractions can cause articulation problems, which may or may not be correctible by speech therapy. Finally, indications point to these extractions as a cause of temporal mandibular joint dysfunction later in life.

In the same manner that dentistry in general has attempted to eschew extraction except as an extreme measure, orthodontic practice should develop techniques that treat extraction as the exception rather than the rule. Such a technique forms the basis for the present invention.

SUMMARY OF THE INVENTION

It is therefore an object of the invention to provide a system of orthodontic appliances that can operate to increase space in a dental arch without extraction.

A further object of the invention is a method for increasing space in a dental arch without extraction.

Yet another object of the invention is a system of orthodontic appliances that combine the effects of a palatal expander bar, an extraoral force device, and a lip bumper, to provide arch expansion for both the maxillary and mandibular arches.

These and other objects are achieved in the present invention, which addresses both a system of orthodontic appliances and a method for their use. Increased space in the maxillary arch is gained by the use of a transpalatal bar. The transpalatal bar means includes adjustable palatal wire means, the ends of the palatal wire means being received in maxillary lingual sheaths carried on a pair of maxillary molars. The wire receiving portions of these lingual sheaths are mesially offset by about eight degrees. The mandibular expansion means includes lip bumper means extending around the periphery of the mandibular arch without making contact with the teeth thereof, with the distal ends of the lip bumper means being received into the bumper receiving portion of mandibular buccal tube means carried on two mandibular molars. The bumper receiving portions are mesially offset by about five degrees.

The system may further include extraoral force means, including headgear means for applying a specified force to selected teeth, with the distal ends thereof received into maxillary buccal tubes carried on two maxillary molars.

A method of gaining space in a dental arch according to the invention includes the steps of rotating and distally moving the first molars by application of a rotational and distal force through orthodontic appliances carried on a pair of molars. The rotating and moving force is transmitted to the molars through appliance receiving means having a mesial offset. Further distal movement may be obtained by the step of applying a distal force to the maxillary first molars by an extraoral force means. It should be noted that this method specifically does not include the step of extracting teeth in order to gain space within the arch.

BRIEF DESCRIPTION OF THE DRAWINGS

FIG. 5 is a plan view of a portion of a maxillary arch, illustrating employment transpalatal bar of the present invention simultaneously on two pairs of molars;

FIG. 6 is a pictorial representation of a maxillary buccal tube according to the invention;

DETAILED DESCRIPTION OF PREFERRED EMBODIMENTS

Figure 1A:
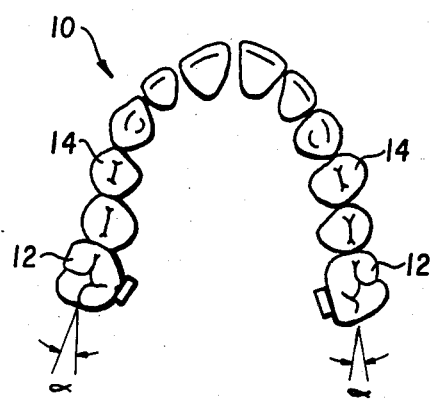
FIGS. 1(a) and (b) are plan views of a maxillary arch before and after treatment according to the present invention, respectively.
Figure 1B:
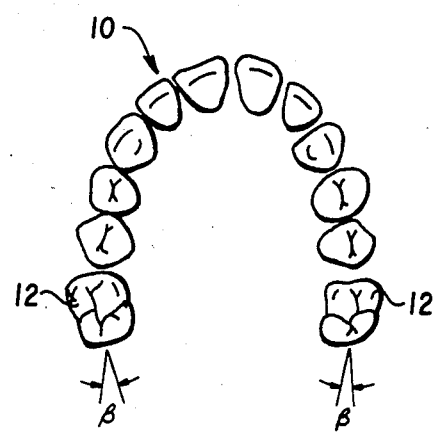

The present invention rests upon the discovery that most cases of malocclusion stem from improper rotation of the molars. Correction of that condition has been found to provide significant increase in arch span, often in excess of 1.5 mm/quadrant, or 3.0 mm/arch. The condition and its solution are seen in FIGS. 1(a) and (b), showing a maxillary arch 10 before and after treatment according to the invention. In FIG. 1(a), the typical "crowded" arch is seen. It should be noted that the centerline of the first molars 12 is tilted mesio-lingually by an angle alpha. Normal practice in this situation would call for the extraction of first bicuspids 14 (as well as their mandibular counterparts) before proceeding with further treatment. The present invention, in contrast, achieves the results seen in FIG. 1(b) without extraction. There, it can be observed, the first molars have been rotated, so that their centerlines are sloped disto-buccally by an angle beta. It should also be noted that molars 12 have been moved distally, opening the arch. It has been found that provision of such space allows the anterior portion of the arch to "fall into place" in the course of normal growth, requiring little to no orthodontic treatment to achieve proper alignment.

The present invention contemplates the combined utilization of several methods and appliances to achieve expansion of both the maxillary and mandibular arches without extraction. In general, the expansion of the maxillary arch is achieved by the use of a transpalatal bar, employing a maxillary lingual sheath modified as detailed below, together with a extraoral force ("EOF") appliance, again utilizing specially designed appliances. Mandibular arch expansion is accomplished by using the facial musculature, acting through a special lip bumper means upon the mandibular molars. The method can achieve additional results though further combination of appliances, as will be discussed.

Figure 2:
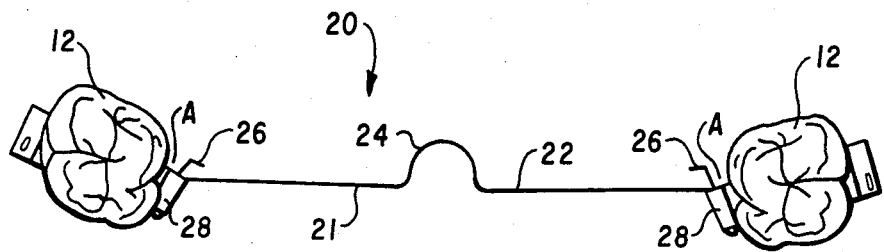
FIG. 2 is a plan view of a portion of a maxillary arch, illustrating the transpalatal bar of the present invention.

The transpalatal bar 20 of the present invention is shown in FIG. 2. Such devices are generally known in the art. As with known devices, the transpalatal bar of the invention includes a wire 21, chosen for its ability to exert a resilient spring-like force when bent, with a loop 24 formed in the center of same and having ends 26 bent double to form a convenient means for attaching the wire to lingual sheaths 28 mounted lingually on first molars 12.

Figure 3:
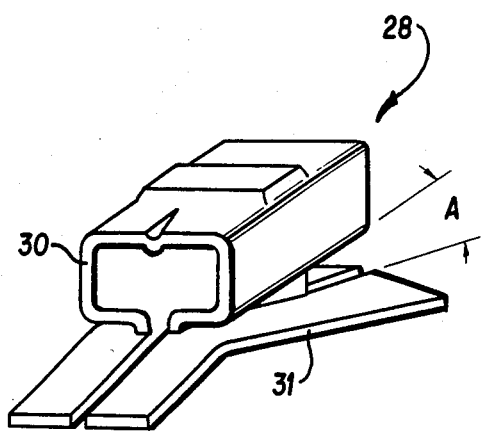
FIG. 3 is a pictorial representation of a maxillary lingual sheath according to the present invention.

Although such devices have been used for some time, the manner in which the art has employed them cannot meet the needs of the present technique. Normally, the lingual sheaths known to the art are mounted on the disto-lingual cusps of the first molars, and a transpalatal bar cannot be inserted into the sheath early in treatment due to the rotation of these molars. As seen in FIG. 3, however, the present invention solves that problem by providing a lingual sheath 28 whose receiving portion 30 is offset from the plane of the band 31 by an angle A, preferably about 8 degrees. Referring again to FIG. 2, the lingual sheath is carried on the tooth with the offset of each sheath toward the mesial. This orientation permits easy installation of the transpalatal bar at an early stage of treatment to effect the molar rotation of the invention.

Figure 4:
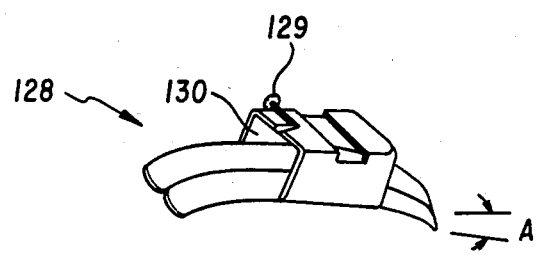
FIG. 4 is a pictorial representation of an alternate embodiment of a maxillary lingual sheath according to the present invention.

An alternate embodiment 128 of the lingual sheath of the invention is shown in FIG. 4. The receiving portion 130 of this embodiment is mesially offset by angle A, as discussed above, but also a gingival hook 129 is provided. This additional portion of the sheath can serve to carry an elastic, if needed, or it can be used to tie the transpalatal bar securely into the lingual sheath, to prevent accidental dislodging of the appliance.

An advantage of the present invention is the ability to perform the technique on adjacent molars, if the patient's second molars have erupted. Seen in FIG. 5, this variation of the method calls for the employment of two transpalatal bars 20, one affixed to each first molar 12 and the other identically fixed to each second molar 13. To coordinate the rotation pattern, buccal wires 32, with appropriate appliances as known in the art, are attached sectional to each pair of adjacent molars.

Figure 7:
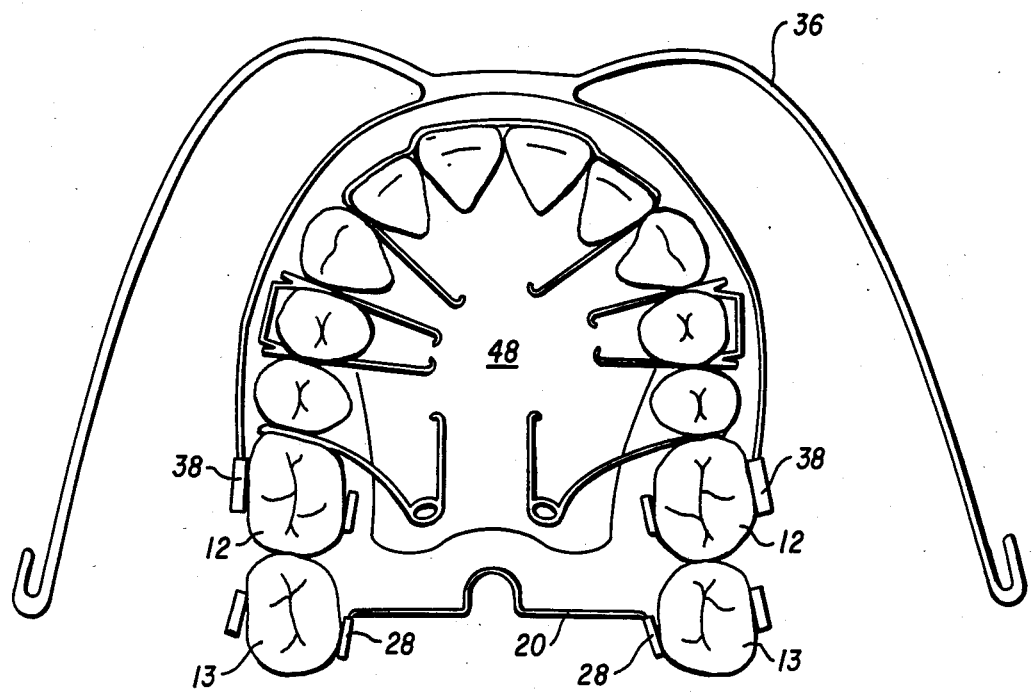
FIG. 7 is a plan view of a maxillary arch, illustrating elements of the invention installed for arch expansion.

Additional distal movement of the molars is gained by utilizing an EOF headgear 36, as shown in FIG. 7. As is known in the art, such headgear provides distal force greater than that possible by the transpalatal bar (on the order of 150 grams), and can be effective to achieve root movement of the tooth. The headgear is attached to the tooth at maxillary buccal tube 38, best seen individually in FIG. 6. Preferably, this tube is a "triple" tube, so called due to the provision for three appliance attachments. A rectangular tube 40 carries the main treatment wire, and an auxiliary tube for the auxiliary wire, and an EOF tube to accept the distal ends of the headgear. Although triple buccal tubes are known in the art, such tubes are not used as seen here. Most such devices are employed in conjunction with the Begg method, or with so-called four-stage techniques, both of which use tubes sequentially, rather than all tubes simulataneously. A post 46 allows for attachment of an elastic, if desired.

An overview of the techniques employed for maxillary spacing is seen in FIG. 7, which shows a transpalatal bar 20 being employed on the second molars 13, with an EOF headgear 36 attached to first molars 12. If needed, additional appliances, such as the removable plate 48, shown with appropriate appliances known in the art, can be employed, both to assist the operation of the transpalatal bar and EOF headgear, or to align the anterior teeth.

Figure 8:
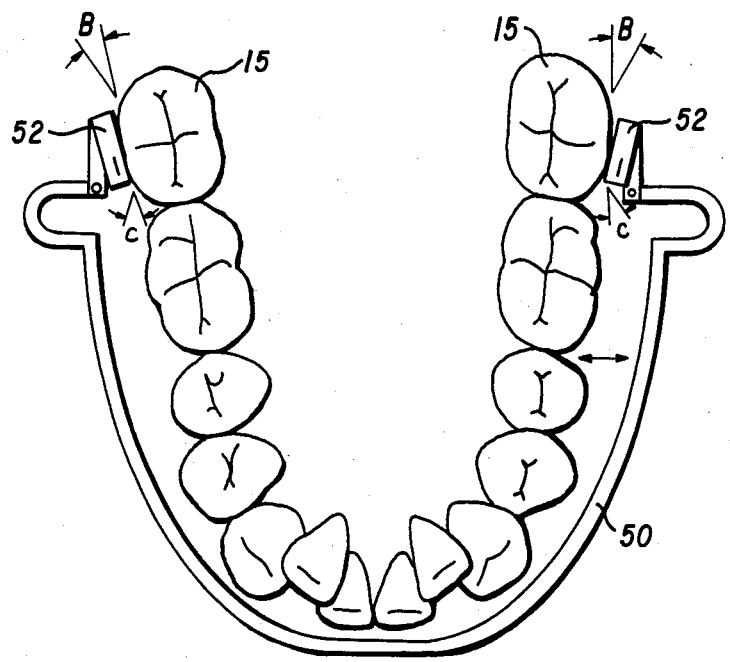
FIG. 8 is a plan view of a mandibular arch, with a lip bumper installed according to the invention.

Gaining space in the mandibular arch is, of course, a different matter entirely, becuase whatever appliance is used, it must leave the tongue free. A solution to that problem is the lip bumper, which applies force derived from the facial muscles to the teeth. As seen in FIG. 8, the lip bumper 50 of the present invention is inserted into mandibular buccal tubes 52 mounted on the second molars 15. The constant force applied by the facial muscles exerts a distally-directed force on the lip bumper, which in turn transmits that force to the tooth.

Figure 9:
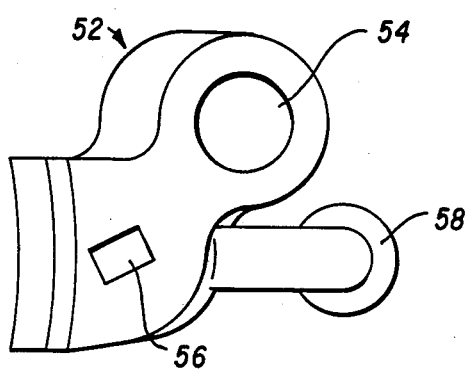
FIG. 9 is a pictorial representation of a lower molar buccal tube according to the invention.

The mandibular buccal tube 52, best seen in FIG. 9, is unique in the orientation of the two passages that extend mesio-distally through the device. Lip bumper receiving passage 54 is offset mesially by an angle B (FIG. 8). This offset operates in the same manner as the mesial offset previously seen in the maxillary lingual sheath, discussed above, to produce the desired rotation of the molars. At the same time, the rectangular passage 56, which carries the archwire from the second bicuspid, is distally offset by an angle C. The latter offset allows proper wire engagement. Preferably, angle B is about five degrees (mesial), and angle C is about four degrees (distal). This buccal tube is shown mounted to the second molars, but of course the identical tube, appropriately dimensioned, could be employed on the first molars. In that case, the tube could be manufactured with a removable cap to facilitate archwire insertion into the second molars. The mandibular buccal tube 52 also includes a post 58 protruding outwardly therefrom and extending in a substantially mesio-distal direction. The post 58 may be used to secure the end of either a lip bumper or archwire, or can be used for the attachment of an elastic.

Those in the art will understand that modifications and variations may be made in the embodiments depicted herein, without departing from the spirit of the invention. For example, the choice of materials is left to those in the art, who will be able to choose from among those materials readily available. Also, the use of other clinical techniques, not mentioned herein, can be combined with the method of the invention to produce therapeutic results in particular cases. These and other departures from the specific disclosure presented above fall within the scope of the invention, which is defined solely by the claims appended hereto.

I claim:

1. A system of orthodontic appliances, comprising:
   at least one transpalatal bar means, including adjustable palatal wire means, the ends of said palatal wire means being received in maxillary lingual sheaths carried on a pair of maxillary molars, the wire receiving portions of said lingual sheaths being mesially offset by about eight degrees; and mandibular expansion means, including lip bumper means extending around the periphery of the mandibular arch without making contact with the teeth thereof, the distal ends of said lip bumper means being received into the bumper receiving portion of mandibular buccal tube means carried on two mandibular molars, said bumper receiving portions being mesially offset by about five degrees.

2. The orthodontic system of claim 1, further comprising:

extraoral force means, including headgear means for applying a specified force to selected teeth, having the distal ends thereof received into maxillary buccal tubes carried on two maxillary molars.

3. The orthodontic system of claim 1, wherein said maxillary lingual sheath includes post means for securing said palatal wire means.

4. A mandibular buccal tube for receiving a lip bumper and an archwire, comprising:

mounting means for securing the tube to a tooth;

lip bumper receiving means for receiving the distal ends of the lip bumper, including a passage extending therethrough in a mesio-distal direction, said passage being mesially offset by an acute angle in relation to said mounting means for facilitating insertion of a lip bumper therein at an early stage of treatment to effect molar rotation; and archwire receiving means for receiving an archwire, including a passage extending therethrough in a mesio-distal direction, said passage being distally offset by an acute angle in relation to said mounting means for facilitating engagement of an archwire therein.

5. The maxillary lingual sheath of claim 9, further comprising post means for securing said transpalatal bar within said passage.

6. The mandibular buccal tube of claim 4, said tube further comprising:

post means protruding outwardly therefrom and extending in a substantially mesio-distal direction.

7. The mandibular buccal tube of claim 4, wherein said passage extending through said lip bumper receiving means is mesially offset by about five degrees; and said passage extending through said archwire receiving means is distally offset by about four degrees.

8. A method for increasing the space within a dental arch, consisting of the steps of:

rotating and distally moving the first molars by application of a rotational and distal force through an orthodontic appliance carried on said molars, said force being simultaneously transmitted in a mesially offset direction through appliance receiving means having a mesial offset and applying a distal force to the maxillary first molars by an extraoral force means.

9. Apparatus for increasing the space within a dentral arch comprising:

(a) a transpalatal bar having distal ends;

(b) a pair of maxillary lingual sheaths mounted on generally opposing molar teeth, each of said sheaths including:

(i) mounting means for securing the sheath to one of said generally opposed molar teeth;

(ii) transpalatal bar receiving means for receiving one of said distal ends, including a passage formed therethrough in a mesio-distal direction, said passage being mesially offset by an acute angle in relation to said mounting means for facilitating insertion therein of one of said distal ends at an early stage of treatment to effect molar rotation; and each of said distal ends being received in a respective one of said passages and extending in a mesially offset direction upon initial insertion in the respective passage.

10. Apparatus according to claim 9, wherein said passage formed through said transpalatal bar receiving means is mesially offset by about eight degrees.

* * * * *